United States Patent [19]
Lai et al.

[11] Patent Number: 5,358,995
[45] Date of Patent: Oct. 25, 1994

[54] SURFACE WETTABLE SILICONE HYDROGELS

[75] Inventors: Yu-Chin Lai, Pittsford; Dominic V. Ruscio, Webster; Paul L. Valint, Jr., Pittsford, all of N.Y.

[73] Assignee: Bausch & Lomb Incorporated, Rochester, N.Y.

[21] Appl. No.: 883,449

[22] Filed: May 15, 1992

[51] Int. Cl.$^5$ .................................. C08F 230/08
[52] U.S. Cl. ......................... 524/547; 525/100; 526/279
[58] Field of Search ............... 524/547; 525/100; 526/279

[56] References Cited

U.S. PATENT DOCUMENTS

| | | | |
|---|---|---|---|
| 3,220,960 | 11/1965 | Wichterle | 260/2.5 |
| 3,408,429 | 10/1968 | Wichterle | 264/1 |
| 3,496,254 | 2/1970 | Wichterle | 264/1 |
| 3,808,178 | 4/1974 | Gaylord | 260/86.1 |
| 4,084,459 | 4/1978 | Clark | 82/1 |
| 4,136,250 | 1/1979 | Mueller | 528/29 |
| 4,153,641 | 5/1979 | Deichert | 260/827 |
| 4,182,822 | 1/1980 | Chang | 526/264 |
| 4,189,546 | 2/1980 | Deichert | 528/26 |
| 4,192,827 | 3/1980 | Mueller | 525/123 |
| 4,195,030 | 3/1980 | Deichert | 260/448.2 |
| 4,197,266 | 4/1980 | Clark | 264/1 |
| 4,254,248 | 3/1981 | Friends | 526/279 |
| 4,260,725 | 4/1981 | Keogh | 526/279 |
| 4,261,875 | 4/1981 | LeBoeuf | 260/29.7 |
| 4,276,402 | 6/1981 | Chromecek | 526/264 |
| 4,486,577 | 12/1984 | Mueller | 525/474 |
| 4,605,712 | 8/1986 | Mueller | 525/474 |
| 4,711,943 | 12/1987 | Harvey | 526/279 |
| 4,780,515 | 10/1988 | Deichert | 526/245 |
| 4,829,137 | 5/1989 | Stoyan | 526/245 |
| 4,954,587 | 9/1990 | Mueller | 526/245 |

FOREIGN PATENT DOCUMENTS

| | | |
|---|---|---|
| 0067254 | 12/1982 | European Pat. Off. |
| 0184924 | 6/1986 | European Pat. Off. |
| 0396364 | 11/1990 | European Pat. Off. |
| 8203397 | 10/1982 | World Int. Prop. O. |
| 8503940 | 9/1985 | World Int. Prop. O. |
| 8601518 | 3/1986 | World Int. Prop. O. |
| 9305098 | 3/1993 | World Int. Prop. O. |

OTHER PUBLICATIONS

"Measuring Oxygen Permeability of Gas Permeable Hard and Hydrogel Lenses and Flat Samples in Air," Irving Fatt, et al., *Int'l Contact Lens Clinic*, vol. 14, No. 10, Oct. 1987.

*Primary Examiner*—Bernard Lipman
*Attorney, Agent, or Firm*—David M. Krasnow

[57] ABSTRACT

A novel silicone-containing, hydrogel material is disclosed comprising an acrylic-capped polysiloxane prepolymer, polymerized with a bulky polysiloxanylalkyl (meth)acrylate monomer and at least one hydrophilic monomer.

21 Claims, No Drawings

SURFACE WETTABLE SILICONE HYDROGELS

BACKGROUND OF THE INVENTION

1. Field of the Invention

The present invention relates to novel polysiloxane water absorbing materials which can be used for biomedical devices, such as, contact lenses and intraocular lenses. These hydrogels can be fashioned into contact lenses that are water absorbing, soft, hydrophilic, flexible, hydrolytically stable and biologically inert. The hydrogels are prepared from the polymerization of an acrylic-capped polysiloxane prepolymer with a bulky polysiloxanylalkyl (meth)acrylate monomer and at least one hydrophilic monomer.

2. Background

Hydrogels have long been a desirable class of material for the preparation of biomedical devices. See, for example, Wichterle, et al U.S. Pat. No. 3,220,960 which discloses hydrogels comprising a hydrated polymer of a hydroxyalkyl acrylate or methacrylate crosslinked with a corresponding diester (poly 2-hydroxyethyl methacrylate, known as poly-HEMA).

Hydrogels are crosslinked polymeric systems that can absorb and retain water. The physical properties of hydrogels can vary widely and are mostly determined by their water content. Since hydrogels exhibit excellent biocompatibility, there has been extensive interest in the use of hydrogels for biomedical devices, especially contact lenses.

In the field of contact lenses, various factors must combine to yield a material that has appropriate characteristics. Oxygen permeability, wettability, material strength and stability are but a few of the factors which must be carefully balanced to achieve a useable contact lens. Since the cornea receives its oxygen supply exclusively from contact with the atmosphere, good oxygen permeability is a critical characteristic for any contact lens material. Wettability also is important in that, if the lens is not sufficiently wettable, it does not remain lubricated and therefore cannot be worn comfortably in the eye. The optimum contact lens would therefore, have both excellent oxygen permeability, and excellent tear fluid wettability.

Polymeric materials that can be polymerized to form a water-free xerogel are known. Xerogels are understood to be (unhydrated) polymers which swell in the presence of water and retain their water content (i.e., they can be hydrated to form hydrogels). It is also known, with respect to hydrogel materials traditionally used to make contact lenses, that as water content of the crosslinked hydrogel polymers increases, so does the oxygen permeability through the lens to the eye and its cornea. However, as the water content of hydrogel contact lenses exceeds 70% water by weight, certain mechanical characteristics are compromised, thus limiting the oxygen permeability practically achievable in such systems. For example, high-water materials tend to exhibit tearing or other breakage as a result of poor tensile strength. What has accordingly been sought is a highly oxygen permeable material that is also durable and highly wettable.

Silicone-containing materials have been pursued toward this end. While they display very good oxygen permeability and durability, most silicone-containing materials are largely hydrophobic and therefore not sufficiently wettable.

As disclosed in U.S. Pat. No. 4,153,641, various hydrophobic silicone-containing prepolymers such as 1,3-bis(methacryloxyalkyl)-polysiloxanes have been modified by some known hydrophilic monomers such as 2-hydroxyethyl methacrylate (HEMA). However, the resultant contact lenses had a low water content level, and tended to be too stiff to be used as a hydrogel (modulus value over 300 g/mm$^2$).

Therefore, there remains a need for contact lens material having the high oxygen permeability characteristics of a polysiloxane-containing prepolymer, yet having a modulus low enough to be used as a hydrophilic hydrogel formulation. Such a formulation would be particularly advantageous as a contact lens material.

SUMMARY OF THE INVENTION

In accordance with the present invention, new silicone-containing, hydrogel materials are disclosed comprising an acrylic ester-capped polysiloxane prepolymer, polymerized with a bulky polysiloxanylalkyl (meth)acrylate monomer, and at least one hydrophilic monomer. The polymers of the present invention can be used to produce highly wettable hydrogels with ideal rigidity, oxygen permeability and other physical properties. Such silicone-containing hydrogels are well-suited for use as biomedical devices such as contact lenses.

The hydrogels of the present invention are formed from the polymerization product of:

(a) an acrylic-capped polysiloxane prepolymer represented by the formula:

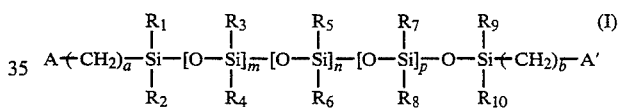

wherein:

A and A' are independently an ester or amide of an acrylic or a methacrylic acid;

$R_1$–$R_{10}$ are independently an alkyl-, ether-, alcohol-, fluoroalkyl-, fluoroether-containing group having 1 to 10 carbons or an aromatic-containing group having 6–18 carbons;

m, n, and p are independently 0 to 200 with m+n+p being from 2 to 200; and a and b are independently 1 to 10;

(b) a bulky polysiloxanylalkyl (meth)acrylate monomer represented by the formula:

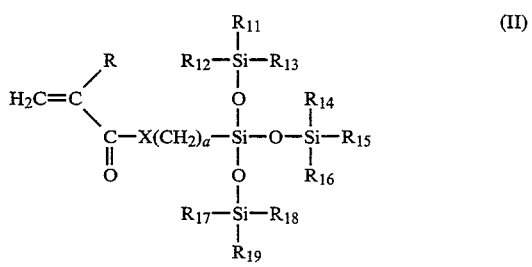

wherein:

X is O or N—R;

R is H or CH$_3$;

$R_{11}$–$R_{19}$ are independently an alkyl-, fluoroalkyl-, alcohol-, ether-, fluoroether-containing group having 1-10 carbons, or an aromatic-containing group having 6–18 carbons; and a is 1, or 3 to 10; and (c) at least one hydrophilic monomer.

DETAILED DESCRIPTION OF THE INVENTION

The crosslinked polymeric network found in the hydrogels of the present invention are believed to be formed, in part, from the polysiloxane prepolymer α,ω bonded through a divalent hydrocarbon group to a polymerized activated unsaturated group. When the term "activated" is used with the term "unsaturated group" herein, it is meant that an unsaturated group which is activated is one which has a substituent which facilitates free radical polymerization. These activated unsaturated groups are polymerized to form the polymers of the present invention. Preferably the activating groups lend themselves to polymerization under mild conditions, such as, ambient temperatures.

Notations such as "(meth)acrylate" or "(meth) acrylamide" are used herein to denote optional methyl substitution. Thus, for example, methyl (meth)acrylate includes both methyl acrylate and methyl methacrylate and N-alkyl(meth)acrylamide includes both N-alkyl acrylamide and N-alkyl methacrylamide.

The term "prepolymer" denotes a high molecular weight monomer containing at least two polymerizable groups. Polymerization of prepolymers with other monomers as described herein produces polymers having a crosslinked, three dimensional network which can be used to produce wettable hydrogels with good rigidity, oxygen permeability and other physical properties. These silicone-containing hydrogels are well-suited for use as biomedical devices such as contact lenses.

The present invention contemplates polymerizing acrylic-capped polysiloxane prepolymers with bulky polysiloxanylalkyl (meth)acrylate monomers and at least one hydrophilic monomer.

Preferred acrylic-capped polysiloxane prepolymers of the present invention are those having from about 2 to about 200 repeating dimethylsiloxane units, such as α,ω-Bis(methacryloxyalkyl) polysiloxane, and is most preferably α,ω-Bis(methacryloxybutyl)dimethylsilyl polysiloxane which has about 25 repeating dimethylsiloxane units such that, in Formula I, m+n+p is equal to about 25.

Preferred bulky polysiloxanylalkyl (meth)acrylate (TRIS-type) monomers include methacryloxypropyl tris(trimethylsiloxy) silane, pentamethyldisiloxanylmethylmethacrylate, tris(trimethylsiloxy)methacryloxy propylsilane, phenyltetramethyldisiloxanylethyl acrylate, and methyldi(trimethylsiloxy)methacryloxymethyl silane, with methacryloxypropyl tris(trimethylsiloxy) silane being the most preferred.

Preferred hydrophilic monomers may be either acrylic- or vinyl-containing. Such hydrophilic monomers may themselves be used as crosslinking agents. The term "vinyl-type" or "vinyl-containing" monomers refers to monomers containing the vinyl grouping (CH$_2$=CH$_2$), and are generally highly reactive. Such hydrophilic vinyl-containing monomers are known to polymerize relatively easily. "Acrylic-type" or "acrylic-containing" monomers are those monomers containing the acrylic group

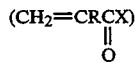

wherein

R=H or CH$_3$ and

X=O or NH, which are also known to polymerize readily.

Preferred hydrophilic vinyl-containing monomers which may be incorporated into the hydrogels of the present invention include monomers such as N-vinyl lactams (e.g. N-vinyl pyrrolidone (NVP)), N-vinyl-N-methyl acetamide, N-vinyl-N- ethyl acetamide, N-vinyl-N-ethyl formamide, N-vinyl formamide, with NVP being the most preferred.

Preferred hydrophilic acrylic-containing monomers which may be incorporated into the hydrogel of the present invention include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, with DMA being the most preferred.

When both an acrylic-containing monomer and a vinyl-containing monomer are incorporated into the invention, a further crosslinking agent having both a vinyl and an acrylic polymerizable group may be used, such as the crosslinkers which are the subject of presently co-pending and commonly assigned U.S. patent application No. 07/788,071 filed Nov. 5, 1991, now abandoned, the entire content of which is incorporated by reference herein. Such crosslinkers help to render the resulting copolymer totally UV-curable. However, the copolymer could also be cured solely by heating, or with a combined UV and heat regimen. Photo and/or thermal initiators required to cure the copolymer will be included in the monomer mix, as is well-known to those skilled in the art.

Other crosslinking agents which may be incorporated into the silicone-containing hydrogel of the present invention include polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N,N'-dihydroxyethylenebisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, mannitol, and sorbitol. Further, illustrations include N,N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM) as disclosed in U.S. Pat. No. 4,954,587.

Other known crosslinking agents are polyetherbisurethane-dimethacrylates as described in U.S. Pat. No. 4,192,827, and those crosslinkers obtained by reaction of polyethylene glycol, polypropylene glycol and polytetramethylene glycol with 2-isocyanatoethyl methacrylate (IEM) or m-isopropenyl-γ,γ,-dimethylbenzyl isocyanates (m-TMI), and polysiloxane-bisurethane-dimethacrylates as described in U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

The hydrogels of this invention are silicone-containing hydrogels formed from monomer mixtures comprising an acrylic-capped polysiloxane prepolymer (preferably α,ω-Bis(methacryloxyalkyl) polysiloxane), a bulky polysiloxanylalkyl (meth)acrylate monomer (preferably methacryloxypropyl tris(trimethylsiloxy) silane (TRIS)), and hydrophilic monomers. While individual, silicone-containing components of the monomer mix may have been used together to produce rigid gas permeable lenses of high modulus, it has now surprisingly been found that these components can be incorporated to produce an excellent hydrogel material of low modulus (below about 300 g/mm$^2$). In fact, the combination of the prepolymer with the TRIS-type monomer created hydrogels having properties that could not have been achieved using just one of these two polysiloxane-containing components.

The preferred range of combined polysiloxane prepolymer and bulky polysiloxanylalkyl (meth)acrylate monomers to total monomers is from about 5 to about 80 weight percent, more preferably about from about 20 to about 70 weight percent, and is most preferably 60 weight percent. The weight ratio of polysiloxane prepolymer to the bulky polysiloxanylalkyl (meth)acrylate monomer preferably ranges from about 11:1 to about 1:11, and is more preferably from about 2:1 to about 1:8, and is most preferably from about 1:1 to about 1:4.

Both vinyl-containing and acrylic-containing hydrophilic monomers may be present in the formulation that is the subject of the present invention. When this is the case, the preferred range of the combined vinyl- and acrylic-containing hydrophilic monomer concentration is from about 5 weight percent of the polymeric hydrogel mix to about 80 weight percent, more preferably from about 10 weight percent to about 70 weight percent, and most preferably from about 30 to about 60 weight percent. The weight ratio of vinyl-containing monomer to acrylic-containing monomer is from about 99:1 to about 1:99, and is preferably from about 4:1 to 1:1 when both types of hydrophilic monomers are present.

When either only one of the acrylic- or vinyl-containing hydrophilic monomer is present in the hydrogel, the preferred range of the hydrophilic monomer concentration is from about 5 weight percent of the polymeric hydrogel mix to about 80 weight percent, more preferably from about 10 weight percent to about 60 weight percent, and is most preferably from about 10 to about 40 weight percent.

The monomer mixes employed in this invention, can be readily cured to cast shapes by conventional methods such as UV polymerization, or thermal polymerization, or combinations thereof, as commonly used in polymerizing ethylenically unsaturated compounds. Representative free radical thermal polymerization initiators are organic peroxides, such as acetal peroxide, lauroyl peroxide, decanoyl peroxide, stearoyl peroxide, benzoyl peroxide. tertiarybutyl peroxypivalate, peroxydicarbonate, and the like, employed in a concentration of about 0.01 to 1 percent by weight of the total monomer mixture. Representative UV initiators are those known in the field such as, benzoin methyl ether, benzoin ethyl ether, Darocure 1173, 1164, 2273, 1116, 2959, 3331 (EM Industries) and Igracure 651 and 184 (Ciba-Geigy).

Polymerization of the crosslinker of this invention with other comonomers is generally performed in the presence of a diluent. The polymerization product will then be in the form of a gel. If the diluent is nonaqueous, the diluent must be removed from the gel and replaced with water through the use of extraction and hydration protocols well known to those skilled in the art.

It is also possible to perform the polymerization in the absence of diluent to produce a xerogel. These xerogels may then be hydrated to form the hydrogels as is well known in the art.

In addition to the above-mentioned polymerization initiators, the copolymer of the present invention may also include other monomers as will be apparent to one skilled in the art. For example, the monomer mix may include colorants, or UV-absorbing agents such as those known in the contact lens art.

The polymers of this invention can be formed into contact lenses by spincasting processes (such as those disclosed in U.S. Pat. Nos. 3,408,429 and 3,496,254), cast molding, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The hydrogels the present invention are oxygen transporting, hydrolytically stable, biologically inert, and transparent. The monomers and prepolymers employed in accordance with this invention, are readily polymerized to form three dimensional networks which permit the transport of oxygen and are optically clear, strong and hydrophilic.

The relative softness or hardness of the contact lenses fabricated from the resulting polymer of this invention can be varied by deceasing or increasing the molecular weight of the polysiloxane prepolymer end-capped with the activated unsaturated group or by varying the percent of the comonomer. As the ratio of polysiloxane units to end-cap units increases, the softness of the material increases.

In addition to contact lenses, materials of this invention can be used for the fabrication of prostheses such as heart valves, intraocular lenses, and other biomedical devices.

The terms "shaped articles for use in biomedical applications" or "biomedical devices or materials" mean the hydrogel materials disclosed herein have physicochemical properties rendering them suitable for prolonged contact with living tissue, blood and the mucous membranes.

The following examples serve only to further illustrate aspects of the present invention and should not be construed as limiting the invention.

EXAMPLE 1

Preparation of 1,3-Bis(4-methacryloxybutyl) tetramethyldisiloxane 1,3-Bis (4-hydroxybutyl) tetramethyldisiloxane (557 g), dry pyridine (634 g) and 2 liters of hexane were charged to a 5-liter reaction flask equipped with a mechanical stirrer and drying tube. The mixture was cooled to 0 degrees C. and then 836 g of methacryloyl chloride was added dropwise. The mixture was stirred overnight. The mixture was then extracted consecutively with 10% aqueous solutions of HCl and NH$_3$ to remove excess reagents and chloride. The resulting solution was dried with dry magnesium sulfate and the solvent was removed under reduced pressure. Approximately 480 g of the named product was recovered. The product identity was confirmed using proton NMR.

EXAMPLE 2

Preparation of α,ω-Bis (methacryloxybutyl) dimethylsilyl polysiloxane ($M_2D_{25}$)

Octamethylcyclotetrasiloxane (D4) (61.44 g) and 1,3-Bis(4-methacryloxybutyl)tetramethyldisiloxane (10.25 g) as prepared in Example 1, and 1.5 ml of triflic acid were charged into a reaction flask equipped with a mechanical stirrer. The mixture was stirred at 60 degrees C. while under a nitrogen blanket for two days. The mixture was then diluted with hexane and neutralized with sodium carbonate. The mixture was then washed with water, and dried with dry magnesium sulfate. The solvent was removed under reduced pressure and low molecular weight volatiles were removed at 110 degrees C. at 0.2 mm Hg. The named product has about 25 repeating dimethylsiloxy units added through the reaction.

EXAMPLE 3

Preparation of α,ω-Bis(methacryloxybutyl)dimethylsilyl polysiloxane ($M_2D_{200}$)

This prepolymer was prepared followed by the same procedure as described in Example 2 except that 490 grams of D4 was used. The product has about 200 repeating dimethylsiloxy units added through the reaction.

EXAMPLES 4–13

Formulations of the Hydrogel with Varying Ratios

As shown in Tables 1 and 2, varying formulations of the invention comprising the following substituents were prepared: α,ω-Bis(methacryloxyalkyl)polysiloxane and methacryloxypropyl tris(trimethylsiloxy) silane (TRIS)—a total of 60 parts; N,N-dimethyl acrylamide (DMA) and N-vinyl pyrrolidone (NVP)—a total of 40 parts. Each formulation contained a constant amount of hexanol as solvent (40 parts) and Darocur-1173 as a photoinitiator (0.2 part). Examples 4, 5 and 16 contained no TRIS and are provided as comparative examples. Further, Example 12 and 13 contained no $M_2D_{25}$ and are provided for comparative purposes only. The formulations which contained both DMA and NVP also contained 0.1 part of methacryloxyethyl vinyl carbonate as an additional crosslinking agent. All formulations were UV-cured between two glass plates for two (2) hours at room temperature. The resultant films were isolated, followed by extraction with ethanol for sixteen (16) hours and boiling water hydration for four (4) hours, then placed in phosphate buffered saline. The ratios of the various substituents were varied, with the resulting properties noted.

The water contents and ethanol extractibles for films cast according to the procedures set forth above were measured gravimetrically. The tensile and tear properties were determined in buffered saline, according to the standard ASTM procedures 1708 and 1938 respectively. The oxygen permeabilities were determined by polargraphic methods taking the edge effect into consideration. (See Fatt, Rasson and Melpolder, Int'l. Contact Lens Clinic, 14, 389 (1987)).

Table 1—Hydrogel Formulations

The following Table 1 shows the varying formulations used in Examples 4–13 of the four preferred components.

TABLE 1

| Formulation | Example # | | | | | | | | | |
|---|---|---|---|---|---|---|---|---|---|---|
| (parts) | 4 | 5 | 6 | 7 | 8 | 9 | 10 | 11 | 12 | 13 |
| M2D25 | 60 | 60 | 30 | 30 | 13 | 13 | 5 | 5 | 0 | 0 |
| TRIS | 0 | 0 | 30 | 30 | 47 | 47 | 55 | 55 | 60 | 60 |
| DMA | 40 | 10 | 40 | 10 | 40 | 10 | 40 | 10 | 40 | 10 |
| NVP | 0 | 30 | 0 | 30 | 0 | 30 | 0 | 30 | 0 | 30 |

TABLE 2

Measured Properties of the Cast Films
The measured physical properties of the films cast from the formulations achieved in Examples 4–13 are provided in Table 2.

| Properties | Example # | | | | | | | | | |
|---|---|---|---|---|---|---|---|---|---|---|
| | 4 | 5 | 6 | 7 | 8 | 9 | 10 | 11 | 12 | 13 |
| % Extract | 3.9 | 10.6 | 10.0 | 8.9 | 1.5 | 9.6 | 8.1 | 12.0 | — | 10.8 |
| % Water | — | 30 | 29 | 28 | 29 | 34 | 34 | 43 | — | 40 |
| Oxy perm, DK | — | 151 | 99 | 108 | 97 | 113 | 81 | 86 | — | 67 |
| Tensile Modulus g/mm2 | — | 570 | 209 | 465 | 89 | 146 | 39 | 134 | — | — |
| Tear, g/mm | — | 1.6 | 3.9 | 4.0 | 12.0 | 20.8 | 26.6 | 19.7 | — | — |

EXAMPLE 4

Comparative Example—No TRIS

In this formulation no TRIS was present. DMA was the only wetting agent (hydrophilic monomer) present. The following formulation was prepared:

| | |
|---|---|
| $M_2D_{25}$ | 60 parts |
| TRIS | 0 |
| DMA | 40 |
| NVP | 0 |

The following properties were measured:

| | |
|---|---|
| % Extractibles | 3.9 |
| % water | * |
| O2 Perm. (Dk) | * |
| Tensile Modulus (g/mm²) | * |
| Tear Strength (g/mm²) | * |

*The resulting film cast from this formulation was weak and could not be fully characterized.

EXAMPLE 5

Comparative Example—No TRIS

This formulation contained no TRIS, but both NVP and DMA were present along with 0.1 part of methacryloxyethyl vinyl carbonate as a crosslinking agent.

| | |
|---|---|
| $M_2D_{25}$ | 60 parts |
| TRIS | 0 |
| DMA | 10 |
| NVP | 30 |

The following properties were measured:

| | |
|---|---|
| % Extractibles | 10.6 |
| % water | 30 |
| $O_2$ Perm. (Dk) | 151 |
| Tensile Modulus (g/mm$^2$) | 570 |
| Tear Strength (g/mm$^2$) | 1.6 |

EXAMPLE 6

In this formulation, 30 parts of $M_2D_{25}$ and TRIS were present.

| | |
|---|---|
| $M_2D_{25}$ | 30 parts |
| TRIS | 30 |
| DMA | 40 |
| NVP | 0 |

The following properties were measured:

| | |
|---|---|
| % Extractibles | 10.0 |
| % water | 29 |
| $O_2$ Perm. (Dk) | 99 |
| Tensile Modulus (g/mm$^2$) | 209 |
| Tear Strength (g/mm$^2$) | 3.9 |

EXAMPLE 7

The following formulation was prepared, cast into films and tested:

| | |
|---|---|
| $M_2D_{25}$ | 30 parts |
| TRIS | 30 |
| DMA | 10 |
| NVP | 30 |

The following properties were measured:

| | |
|---|---|
| % Extractibles | 8.9 |
| % water | 28 |
| $O_2$ Perm. (Dk) | 108 |
| Tensile Modulus (g/mm$^2$) | 465 |
| Tear Strength (g/mm$^2$) | 4.0 |

EXAMPLE 8

The following formulation was prepared, cast into films and tested:

| | |
|---|---|
| $M_2D_{25}$ | 13 parts |
| TRIS | 47 |
| DMA | 40 |
| NVP | 0 |

The following properties were measured:

| | |
|---|---|
| % Extractibles | 1.5 |
| % water | 29 |
| $O_2$ Perm. (Dk) | 97 |
| Tensile Modulus (g/mm$^2$) | 89 |
| Tear Strength (g/mm$^2$) | 12.0 |

EXAMPLE 9

The following formulation was prepared, cast into films and tested:

| | |
|---|---|
| $M_2D_{25}$ | 13 parts |
| TRIS | 47 |
| DMA | 10 |
| NVP | 30 |

The following properties were measured:

| | |
|---|---|
| % Extractibles | 9.6 |
| % water | 34 |
| $O_2$ Perm. (Dk) | 113 |
| Tensile Modulus (g/mm$^2$) | 146 |
| Tear Strength (g/mm$^2$) | 20.8 |

EXAMPLE 10

The following formulation was prepared, cast into films and tested:

| | |
|---|---|
| $M_2D_{25}$ | 5 parts |
| TRIS | 55 |
| DMA | 40 |
| NVP | 0 |

The following properties were measured:

| | |
|---|---|
| % Extractibles | 8.1 |
| % water | 34 |
| $O_2$ Perm. (Dk) | 81 |
| Tensile Modulus (g/mm$^2$) | 39 |
| Tear Strength (g/mm$^2$) | 26.6 |

EXAMPLE 11

The following formulations were prepared, cast into films and tested:

| | |
|---|---|
| $M_2D_{25}$ | 5 parts |
| TRIS | 55 |
| DMA | 10 |
| NVP | 30 |

The following properties were measured:

| | |
|---|---|
| % Extractibles | 12.0 |
| % water | 43 |
| $O_2$ Perm. (Dk) | 86 |
| Tensile Modulus (g/mm$^2$) | 134 |
| Tear Strength | 19.7 |

EXAMPLE 12

Comparative Example—No $M_2D_x$

The following formulation was prepared but could not be successfully cast into films for evaluation:

| | |
|---|---|
| $M_2D_{25}$ | 0 parts |
| TRIS | 60 |
| DMA | 40 |
| NVP | 0 |

EXAMPLE 13

Comparative Example—No $M_2D_{25}$

The following formulation was prepared cast into films and tested.

| | |
|---|---|
| $M_2D_{25}$ | 0 parts |
| TRIS | 60 |
| DMA | 10 |
| NVP | 30 |

The following properties were measured:

| | |
|---|---|
| % Extractibles | 10.8 |
| % water | 40 |
| $O_2$ Perm. (Dk) | 67 |
| Tensile Modulus (g/mm$^2$) | * |
| Tear Strength (g/mm$^2$) | * |

*The films were not strong enough to be tested for modulus or tear characteristics.

EXAMPLE 14

$M_2D_{25}$ Formulation—Low Water Content

The formulation containing the following components was prepared, cured and processed into hydrogel films as those described in Examples 1–10.

| | |
|---|---|
| $M_2D_{25}$ | 35 parts |
| TRIS | 35 |
| DMA | 30 |
| Hexanol | 40 |
| Darocure 1173 | 0.2 |

The following properties were measured:

| | |
|---|---|
| % Extractibles | 3.5 |
| % water | 17 |
| $O_2$ perm. (Dk) | 110 |
| Tensile Modulus (g/mm$^2$) | 134 |
| % Elongation | 148 |
| Tear Strength (g/mm$^2$) | 17 |

EXAMPLE 15

The formulation containing the following components was prepared, cured and processed into hydrogel films as those described in Examples 1–10. This formulation contained one (1.0) part 2-vinyl-4,4-dimethyl-2-oxazolin-5-one (VDMO).

| | |
|---|---|
| $M_2D_{25}$ | 35 parts |
| TRIS | 35 |
| DMA | 30 |
| VDMO | 1.0 |
| Hexanol | 40 |
| Darocure-1173 | 0.2 |

The following properties were measured:

| | |
|---|---|
| % Extractibles | 1.0 |
| % water | 32 |
| $O_2$ Perm. (Dk) | 80 |
| Tensile Modulus (g/mm$^2$) | 86 |
| % Elongation | 140 |
| Tear Strength | 9 |

EXAMPLES 16–19

The following mixes derived from $M_2D_{200}$ as prepared in Example 3 were prepared and processed into hydrogel films by following the same procedures as described in Example 4.

| | Examples | | | |
|---|---|---|---|---|
| Formulation (parts) | 16 | 17 | 18 | 19 |
| $M_2D_{200}$ | 60 | 30 | 15 | 5 |
| TRIS | 0 | 30 | 45 | 55 |
| DMA | 40 | 40 | 40 | 40 |
| Hexanol | 20 | 20 | 20 | 20 |
| Darocur-1173 | 0.2 | 0.2 | 0.2 | 0.2 |

Examples 16–19 were not cured properly and no quality films were obtained.

EXAMPLE 20

Hydrolytic Stability Testing

The cured films produced from the formulation in Example 12, after being extracted with solvent and dried in vacuo, were cut into disks weighing 30 milligrams each (dry weight), with a thickness of 250 microns. The disks were then submerged in buffered saline solution at pH 7.4 in 12 vials and sealed. After equilibration, the films were placed in an oven at 80 degrees C. Three vials were taken out after 3, 5, 7 and 14 days and the dry weight and water contents were determined gravimetrically. The hydrolytic stabilities were reported as percent weight loss over 14 days. Experimentally it was determined that resultant hydrogels with a weight loss of 7 percent or less would be considered stable.

The cured films derived from the formulation described in Example 12 had a measured 14-day weight loss of 5.7% while the water content remained at 32.0%.

EXAMPLE 21

Cast Molding Formulations into Lenses

Monomer mixes derived from formulations shown in Examples 5 and 6 were filtered through a disposable filter (1.2 micron pore size), into a clean vial. Through an applicator, under inert nitrogen atmosphere, 60–90 ul of the monomer mix was injected onto a clean plastic mold. The molds were then compressed and cured for 90 minutes in the presence of UV light (4,200 microwatts). The molds were then opened mechanically and put into a beaker containing aqueous ethanol. The lenses were released from the molds within from 10 minutes to 1 hour. The lenses were then extracted with ethanol for 48 hours, boiled in distilled water for 4 hours and inspected for cosmetic quality and dimension. Lenses passing inspection were thermally disinfected in phosphate buffered saline prior to on-eye evaluation.

EXAMPLE 22

Clinical Evaluations of Hydrogel Lenses

The hydrogel lenses obtained from those described in Example 15 were evaluated on seven human subjects. The lenses were analyzed after a minimum of 4 hours for wettability and surface deposition. The surface wettability rating scale was 0–4 with 0 representing ⅔ of the anterior surface unwetted by the tear film and 4 representing complete wetting. The deposition scale was also 0–4, with 0 representing no surface deposit and 4 representing multiple deposits of 0.5 mm diameter or larger. The following results were obtained:

| $M_2D_{25}$ formulation (Example #) | Wetting | Deposits |
| --- | --- | --- |
| 5 | 3.5 | 1.6 |
| 6 | 3.9 | 1.0 |

Many other modifications and variations of the present invention are possible to the skilled practitioner in the field in light of the teachings herein. It is therefore understood that, within the scope of the claims, the present invention can be practiced other than as herein specifically described.

We claim:

1. A silicone-containing, hydrogel material formed from the polymerization product of a monomer mix comprising:

a) an acrylic-capped polysiloxane prepolymer represented by the formula:

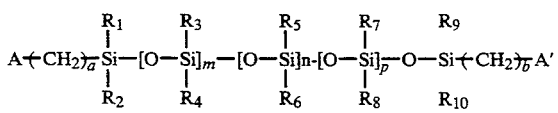

wherein;

A and A' are independently an ester or amide of an acrylic or a methacrylic acid;

$R_1$–$R_{10}$ are independently an alkyl, fluoroalkyl, alcohol, ether, or fluoroether group having 1–10 carbons, or an aromatic group having 6–18 carbons;

m, n, and p are independently 0 to 200 m+n+p being from about 23 to 200; and a and b are independently 1 to 10;

b) a bulky polysiloxanylalkyl (meth)acrylate monomer represented by the formula:

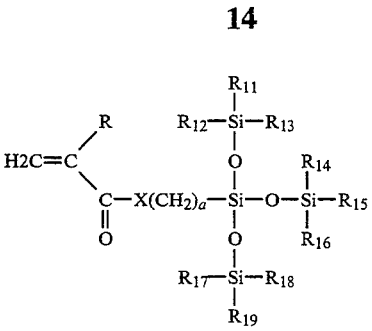

wherein:

X is O or N—R;

R is H or $CH_3$;

$R_{11}$–$R_{19}$ are independently an alkyl, fluoroalkyl, alcohol, ether or fluoroether group having 1–10 carbons, or an aromatic group having 6–18 carbons; and a is 1, or 3 to 10; and c) at least one hydrophilic monomer.

2. The hydrogen of claim 1 wherein said acrylic-capped polysiloxane prepolymer is comprised of a repeating number of between from about 25 to about 200 dimethylsiloxy units.

3. The hydrogel of claim 1 wherein said acrylic-capped polysiloxane prepolymer is an α,ω-Bis(methacryloxy alkyl)dialkylsilylpolysiloxane.

4. The hydrogel of claim 1 wherein said acrylic-capped polysiloxane prepolymer is α,ω-Bis(methacryloxybutyl)dimethylsilylpolysiloxane.

5. The hydrogel of claim 1 wherein said bulky polysiloxanylalkyl (meth)acrylate monomer is selected from the group consisting of pentamethyldisiloxanylmethyl methacrylate, tris(trimethylsiloxy)methacryloxy propylsilane, phenyltetramethyldisiloxanylethyl acrylate, and methyldi(trimethylsiloxy)methacryloxymethylsilane.

6. The hydrogel of claim 1 wherein said bulky polysiloxanylalkyl (meth)acrylate monomer is methacryloxypropyl tris(trimethylsiloxy)silane.

7. The hydrogel of claim 1 wherein said hydrophilic monomer is a vinyl-containing hydrophilic monomer.

8. The hydrogel of claim 7 wherein said vinyl-containing hydrophilic monomer is selected from the group consisting of, N-vinyl-N-methyl acetamide, N-vinylacetamide, N-vinyl-N-methyl formamide, and N-vinyl formamide.

9. The hydrogel of claim 7 wherein said vinyl-containing hydrophilic monomer is an N-vinyl lactam.

10. The hydrogel of claim 7 wherein said vinyl-containing hydrophilic monomer is N-vinyl pyrrolidone.

11. The hydrogel of claim 1 wherein said hydrophilic monomer is an acrylic-containing monomer.

12. The hydrogel of claim 11 wherein said acrylic-type hydrophilic monomer is selected from the group consisting of N,N-dimethyl acrylamide, 2-hydroxyethyl methacrylate, glycerol methacrylate, 2-hydroxymethylacrylamide, methacrylic acid and acrylic acid.

13. The hydrogel of claim 1 wherein said hydrogel comprises both a vinyl-containing hydrophilic monomer and an acrylic-containing hydrophilic monomer.

14. The hydrogel of claim 1 wherein said hydrogel comprises at least one crosslinking agent.

15. The hydrogel of claim 1 wherein said hydrogel comprises α,ω-Bis(methacryloxyalkyl)polysiloxane polymerized with methacryloxypropyl tris(trimethylsiloxy) silane and N,N-dimethyl acrylamide.

16. The hydrogen of claim 1 wherein said hydrogel comprises $\alpha,\omega$-Bis(methacryloxyalkyl)polysiloxane polymerized with methacryloxypropyl tris(trimethylsiloxy)silane, N,N-dimethyl acrylamide, N-vinyl pyrrolidone and at least one crosslinking agent.

17. The hydrogel of claim 1 wherein the polysiloxane prepolymer and bulky polysiloxyanylalkyl (meth)acrylate monomer are present in the monomer mix in relative amounts represented by the ratio range of from about 11:1 to about 1:11.

18. The hydrogel of claim 1 wherein the polysiloxane prepolymer and bulky polysiloxyanylalkyl (meth)acrylate monomer are present in the monomer mix in relative amounts represented by the ratio range of from about 2:1 to about 1:8.

19. The hydrogel of claim 1 wherein the polysiloxane prepolymer and bulky polysiloxyanylalkyl (meth)acrylate monomer are present in the monomer mix in relative amounts represented by the ratio range of from about 1:1 to about 1:4.

20. The hydrogel of claim 1 wherein the monomer mix comprises a hydrophilic monomer in the amount of about 40 weight percent.

21. A silicone-containing, hydrogel material formed from the polymerization product of a monomer mix comprising:

a) an acrylic-capped polysiloxane prepolymer represented by the formula:

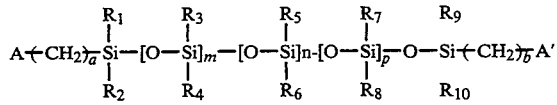

wherein;

A and A' are independently an ester or amide of an acrylic or a methacrylic acid;

$R_1$–$R_{10}$ are independently an alkyl, fluoroalkyl, alcohol, ether, or fluoroether group having 1–10 carbons, or an aromatic group having 6–18 carbons;

m, n, and p are independently 0 to 200 m+n+p being from about 23 to 200; and a and b are independently 1 to 10;

b) a bulky polysiloxanylalkyl (meth)acrylate monomer represented by the formula:

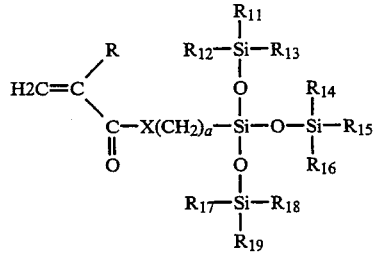

wherein:

X is O or N—R;

R is H or $CH_3$;

$R_{11}$–$R_{19}$ are independently an alkyl, fluoroalkyl, alcohol, ether or fluoroether group having 1–10 carbons, or an aromatic group having 6–18 carbons; and a is 1, or 3 to 10; and c) at least one hydrophilic monomer representing at least 30 to 60 weight percent of the monomer mix.

* * * * *